(12) United States Patent
Brown et al.

(10) Patent No.: US 8,078,492 B2
(45) Date of Patent: Dec. 13, 2011

(54) PROVIDING CONSUMERS WITH INCENTIVES FOR HEALTHY EATING HABITS

(75) Inventors: Michael Wayne Brown, Georgetown, TX (US); Rabindranath Dutta, Austin, TX (US); Michael A. Paolini, Austin, TX (US); Newton James Smith, Jr., Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 2614 days.

(21) Appl. No.: 09/969,298

(22) Filed: Oct. 2, 2001

(65) Prior Publication Data
US 2003/0065561 A1 Apr. 3, 2003

(51) Int. Cl.
*G06Q 30/00* (2006.01)
(52) U.S. Cl. .................. 705/14.1; 235/383
(58) Field of Classification Search .......... 705/14; 463/1
See application file for complete search history.

(56) References Cited

U.S. PATENT DOCUMENTS

| | | | | |
|---|---|---|---|---|
| 4,833,308 | A | * | 5/1989 | Humble ................ 235/383 |
| 4,910,672 | A | | 3/1990 | Off et al. |
| 5,991,376 | A | | 11/1999 | Hennessy et al. |
| 6,077,193 | A | | 6/2000 | Buhler et al. |
| 6,151,586 | A | * | 11/2000 | Brown ................ 705/14 |
| 6,210,272 | B1 | * | 4/2001 | Brown ................ 463/1 |
| 6,440,068 | B1 | | 8/2002 | Brown et al. |
| 6,450,955 | B1 | | 9/2002 | Brown et al. |
| 6,601,016 | B1 | | 7/2003 | Brown et al. |
| 6,618,062 | B1 | | 9/2003 | Brown et al. |
| 6,646,659 | B1 | | 11/2003 | Brown et al. |
| 6,859,215 | B1 | | 2/2005 | Brown et al. |
| 2007/0190501 | A1 | | 8/2007 | Brown et al. |

OTHER PUBLICATIONS

Eicher "Investing in Health Companies tell their workers: "We really care;"" Mar. 28, 1994. Denver Post. p. NOPGCIT.*
Cohen. "Wanted: healthier workes More companies offer rewards for staying well." Jan. 6, 1992. Chicago Tribune. p. 1.*
LaGanga. "New at Vons: Loaves in the Fast Lane." Mar. 7, 1990. Los Angeles Times. vol. 109, Iss. 94, Sec. D, p. 1.*
Staff Reports. "After Hours Event Set." May 6, 1992. Sun Sentinel. p. 3.B.*
Adjusting an Amount Owed for Fueling Based on Vehicle Characteristics, 63 pages, co-pending filing date.
Calculating Taxes Based in Part on Energy Efficiencies Achieved by a Taxpayer, 54 pages, co-pending filing date.
Calculating Corporate Bonuses for Employees Based on Employee Efficiency, 48 pages, co-pending filing date.
Conserving Roadway Lighting, 47 pages, co-pending filing date.
Detailing and Promoting Energy Efficient Products, 49 pages, co-pending filing date.
Promoting Efficient Roadway Usage, 64 pages, co-pending filing date.

(Continued)

*Primary Examiner* — Namrata Boveja
*Assistant Examiner* — Nathan C Uber
(74) *Attorney, Agent, or Firm* — Matthew W. Baca; Amy J. Pattillo (57) ABSTRACT

A method, system, and program for providing consumer healthy habits incentives are provided. A consumable item, consumed by an individual, is detected. A health factor is detected for the consumable item. An electronic incentive is selected for the individual according to the health factor, such that the individual is encouraged to consume a healthy selection of consumable items. An electronic incentive may be further specified according to the individual health history, exercise history and consumption history of an individual.

27 Claims, 6 Drawing Sheets

OTHER PUBLICATIONS

Enabling Transfer of Energy Incentives Between Entities, 51 pages, co-pending filing date.
Providing Incentives for the Purchase of Efficient Vehicles, 43 pages, co-pending filing date.
Adjusting Energy Efficiency Incentives According to Current Energy Efficiency Technology, 48 pages, co-pending filing date.
Long-Term Energy Efficiency Promotion, 60 pages, co-pending filing date.
Remotely Controlling Water Usage, 44 pages, co-pending filing date.
Promoting Heating and Cooling Energy Efficiency, 44 pages, co-pending filing date.

* cited by examiner

| CONSUMABLE ITEM HEALTH INDEX DATABASE | |
|---|---|
| ITEM | HEALTH INDEX |
| FROZEN DINNER A | GRAIN 8<br>MEAT 5<br>DAIRY 2<br>VEGETABLE 8 |
| FROZEN DINNER B | GRAIN 5<br>MEAT 3<br>DAIRY 0<br>VEGETABLE 4 |

FIG. 5

| INCENTIVE STANDARDS DATABASE | | |
|---|---|---|
| INDIVIDUAL | USER A | OVER 50 |
| HEALTH INDEX | INCENTIVE | INCENTIVE |
| GRAIN 8-10 | .25 | .25 |
| MEAT 6-10 | .10 | .15 |
| DAIRY 7-10 | .25 | .20 |
| VEGETABLE 5-10 | .30 | .30 |

PROVIDING CONSUMERS WITH INCENTIVES FOR HEALTHY EATING HABITS

CROSS-REFERENCE TO RELATED APPLICATIONS

The present application is related to the following copending applications, incorporated herein by reference:
(1) U.S. patent application Ser. No. 09/969,068;
(2) U.S. patent application Ser. No. 09/969,319;
(3) U.S. patent application Ser. No. 09/969,055;
(4) U.S. patent application Ser. No. 09/968,801;
(5) U.S. patent application Ser. No. 09/969,365;
(6) U.S. patent application Ser. No. 09/968,919;
(7) U.S. patent application Ser. No. 09/969,166;
(8) U.S. patent application Ser. No. 09/968,779;
(9) U.S. patent application Ser. No. 09/969,093;
(10) U.S. patent application Ser. No. 09/969,280;
(11) U.S. patent application Ser. No. 09/969,255; and
(12) U.S. patent application Ser. No. 09/969,238.

BACKGROUND OF THE INVENTION

1. Technical Field

The present invention relates in general to computer systems and, in particular, to encouraging healthy food habits utilizing computer systems. Still more particularly, the present invention relates to providing electronic incentives for consuming healthy foods.

2. Description of the Related Art

Research continues to show that consumption of healthful foods can decrease chances of acquiring adverse health conditions during life. For example, a diet high in fiber may decrease chances of cancer, organ deterioration, and other digestive diseases.

In particular, where a person is genetically prone to certain adverse health conditions, diet may prolong or stop the onset of the certain adverse health conditions. For example, a person genetically prone to hypoglycemia may reduce the chances of onset by consuming a reduced sugar diet. In another example, a person genetically prone to cancer may consume a diet high in vitamins and vegetables to reduce the chances of cancer.

Particularly since the contents of each food item is required by law to be available to consumers, restaurants and food manufacturers continue to provide consumers with more healthy food choices. However, even with healthy food choices, there is little incentive beyond individual health to make such choices.

Health insurance companies and governments that subsidize health care costs encourage citizens to choose a healthy diet and to exercise to attempt to reduce future health care costs. However, it is difficult for health insurance companies and governments to provide any incentive to citizens to choose healthy diets and exercise, beyond the incentive of better health.

In view of the foregoing, it would be advantageous to provide a method, system, and program for encouraging healthy habits by providing incentives for healthy food purchases. In particular, it would be advantageous to provide a method, system, and program for authorities to provide electronic amount incentives to consumers for healthy food purchases. Further, in view of the foregoing, it would be advantageous to provide a method, system, and program where preferred health is uniquely determined for each consumer.

SUMMARY OF THE INVENTION

In view of the foregoing, it is therefore an object of the present invention to provide an improved computer system.

It is another object of the present invention to provide a method, system and program for encouraging healthy food habits utilizing computer systems.

It is yet another object of the present invention to provide a method, system and program for providing electronic incentives for consuming healthy foods.

According to one aspect of the present invention, a consumable item, consumed by an individual, is detected. A health factor is detected for the consumable item. An electronic incentive is selected for the individual according to the health factor, such that the individual is encouraged to consume a healthy selection of consumable items. The electronic incentive may be further specified according to the individual health history, exercise history and consumption history of an individual.

All objects, features, and advantages of the present invention will become apparent in the following detailed written description.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

DETAILED DESCRIPTION OF THE PREFERRED EMBODIMENT

A method, system, and program for providing electronic incentives for healthy food consumption are provided. For purposes of the present invention, electronic incentives may include, but are not limited to, deductions, vouchers, rebates, electronic coupons, and incentives. In addition, for purposes of the present invention, food may include consumable items selected from fresh, packaged, and prepared foods from markets, restaurants, and other food purveyors. Further, other consumable items, such as medications, may be included. Healthy food, in the present invention, may be designated according to standards provided by an authority, such as the Food and Drug Administration (FDA). Healthy food is preferably further specified according to each consumer's individual health. Consumption of healthy food may be monitored, for example, according to food purchases, food discarded, and food indicated by a consumer to have been eaten. Moreover, whether a food item is considered healthy may vary according to the time of day the food item is consumed and according to the other food items consumed within a particular period of time.

In the following description, for the purposes of explanation, numerous specific details are set forth to provide a thorough understanding of the present invention. It will be apparent, however, to one skilled in the art that the present invention may be practiced without these specific details. In other instances, well-known structures and devices are shown in block diagram form to avoid unnecessarily obscuring the present invention.

Hardware Overview

The present invention may be executed in a variety of systems, including a variety of computing systems and electronic devices under a number of different operating systems. In one embodiment of the present invention, the computing system includes a portable computing system such as a notebook computer, a palmtop computer, a personal digital assistant, a telephone or other electronic computing system that may also incorporate communications features that provide for telephony, enhanced telephony, messaging and information services. However, the computing system may also include, for example, a desktop computer, a network computer, a midrange computer, a server system or a mainframe computer. Therefore, in general, the present invention is preferably executed in a computer system that performs computing tasks such as manipulating data in storage that is accessible to the computer system. In addition, the computer system preferably includes at least one output device and at least one input device.

Figures 1, 2:
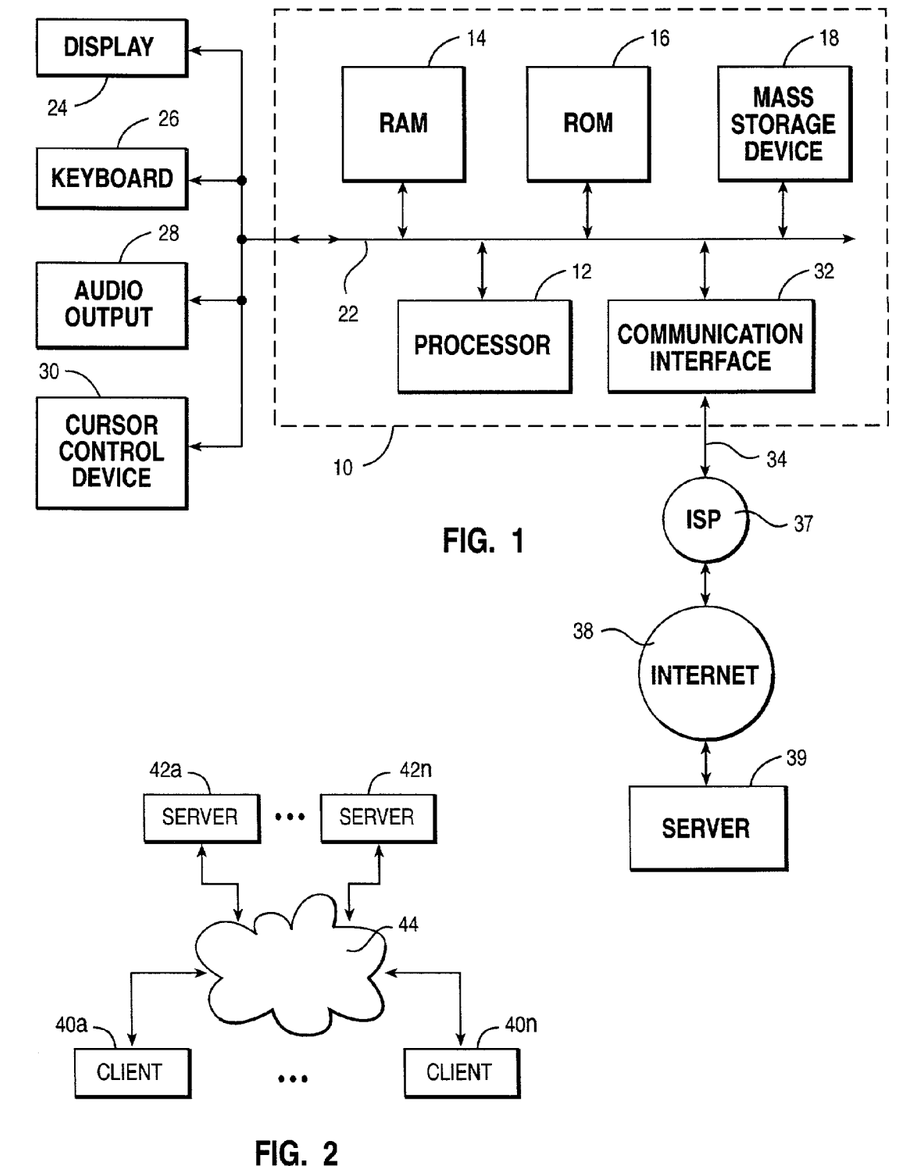
FIG. 1 depicts one embodiment of a computer system with which the method, system and program of the present invention may advantageously be utilized.
FIG. 2 illustrates a simplified block diagram of a client/server environment in which promoting and controlling healthy food consumption may be performed in accordance with the method, system and program of the present invention.

Referring now to the drawings and in particular to FIG. 1, there is depicted one embodiment of a computer system with which the method, system and program of the present invention may advantageously be utilized. Computer system 10 comprises a bus 22 or other communication device for communicating information within computer system 10, and at least one processing device such as processor 12, coupled to bus 22 for processing information. Bus 22 preferably includes low-latency and high-latency paths that are connected by bridges and controlled within computer system 10 by multiple bus controllers.

Processor 12 may be a general-purpose processor such as IBM's PowerpC™ processor that, during normal operation, processes data under the control of operating system and application software stored in a dynamic storage device such as random access memory (RAM) 14 and a static storage device such as Read Only Memory (ROM) 16. The operating system preferably provides a graphical user interface (GUI) to the user. In a preferred embodiment, application software contains machine executable instructions that when executed on processor 12 carry out the operations depicted in the flowcharts of FIGS. 7, 8, and others described herein. Alternatively, the steps of the present invention might be performed by specific hardware components that contain hardwire logic for performing the steps, or by any combination of programmed computer components and custom hardware components.

The present invention may be provided as a computer program product, included on a machine-readable medium having stored thereon the machine executable instructions used to program computer system 10 to perform a process according to the present invention. The term "machine-readable medium" as used herein includes any medium that participates in providing instructions to processor 12 or other components of computer system 10 for execution. Such a medium may take many forms including, but not limited to, non-volatile media, volatile media, and transmission media. Common forms of non-volatile media include, for example, a floppy disk, a flexible disk, a hard disk, magnetic tape or any other magnetic medium, a compact disc ROM (CD-ROM) or any other optical medium, punch cards or any other physical medium with patterns of holes, a programmable ROM (PROM), an erasable PROM (EPROM), electrically EPROM (EEPROM), a flash memory, any other memory chip or cartridge, or any other medium from which computer system 10 can read and which is suitable for storing instructions. In the present embodiment, an example of non-volatile media is storage device 18. Volatile media includes dynamic memory such as RAM 14. Transmission media includes coaxial cables, copper wire or fiber optics, including the wires that comprise bus 22. Transmission media can also take the form of acoustic or light waves, such as those generated during radio wave or infrared data communications.

Moreover, the present invention may be downloaded as a computer program product, wherein the program instructions may be transferred from a remote computer such as a server 39 to requesting computer system 10 by way of data signals embodied in a carrier wave or other propagation medium via a network link 34 (e.g., a modem or network connection) to a communications interface 32 coupled to bus 22. Communications interface 32 provides a two-way data communications coupling to network link 34 that may be connected, for example, to a local area network (LAN), wide area network (WAN), or as depicted herein, directly to an Internet Service Provider (ISP) 37. In particular, network link 34 may provide wired and/or wireless network communications to one or more networks.

ISP 37 in turn provides data communication services through the Internet 38 or other network. Internet 38 may refer to the worldwide collection of networks and gateways that use a particular protocol, such as Transmission Control Protocol (TCP) and Internet Protocol (IP), to communicate with one another. ISP 37 and Internet 38 both use electrical, electromagnetic, or optical signals that carry digital or analog data streams. The signals through the various networks and the signals on network link 34 and through communication interface 32, which carry the digital or analog data to and from computer system 10, are exemplary forms of carrier waves transporting the information.

Further, multiple peripheral components may be added to computer system 10. For example, an audio output 28 is attached to bus 22 for controlling audio output through a speaker or other audio projection device. A display 24 is also attached to bus 22 for providing visual, tactile or other graphical representation formats. A keyboard 26 and cursor control device 30, such as a mouse, trackball, or cursor direction keys, are coupled to bus 22 as interfaces for user inputs to computer system 10. In alternate embodiments of the present invention, additional input and output peripheral components may be added.

Networking Overview

With reference now to FIG. 2, there is depicted a simplified block diagram of a client/server environment in which promoting and controlling healthy food consumption may be performed in accordance with the method, system and program of the present invention. The client/server environment is implemented within multiple network architectures. For example, the architecture of the World Wide Web (the Web) follows a traditional client/server modeled environment.

The terms "client" and "server" are used to refer to a computer's general role as a requester of data (the client) or provider of data (the server). In the Web environment, web browsers such as Netscape Navigator typically reside on client system 40a-40n and render Web documents (pages) served by server systems 42a-42n. Additionally, each of client systems 40a-40n and server systems 42a-42n may function as both a "client" and a "server" and may be implemented utilizing a computer system such as computer system 10 of FIG. 1.

The Web may refer to the total set of interlinked hypertext documents residing on servers all around the world. Network 44, such as the Internet, provides an infrastructure for transmitting these hypertext documents between server systems 42a-42n and client systems 40a-40n. Documents (pages) on the Web may be written in multiple languages, such as Hypertext Markup Language (HTML) or Extensible Markup Language (XML), and identified by Uniform Resource Indicators (URIs) that specify the particular server and pathname by which a file can be accessed, and then transmitted from that server to an end user utilizing a protocol such as Hypertext Transfer Protocol (HTTP). Web pages may further include text, graphic images, movie files, and sounds as well as Java applets and other small embedded software programs that execute when the user activates them by clicking on a link.

It is advantageous in the present invention to utilize both wireless and wired network connections to network 44. Wireless network connections may be implemented utilizing Bluetooth™ or other radio frequency broadcasting. Advantageously, whether wireless or wired network connections are utilized, multiple types of encryption security features may be utilized to protect transmission of personal health information and incentives, as will be understood by one skilled in the art.

Figure 3:
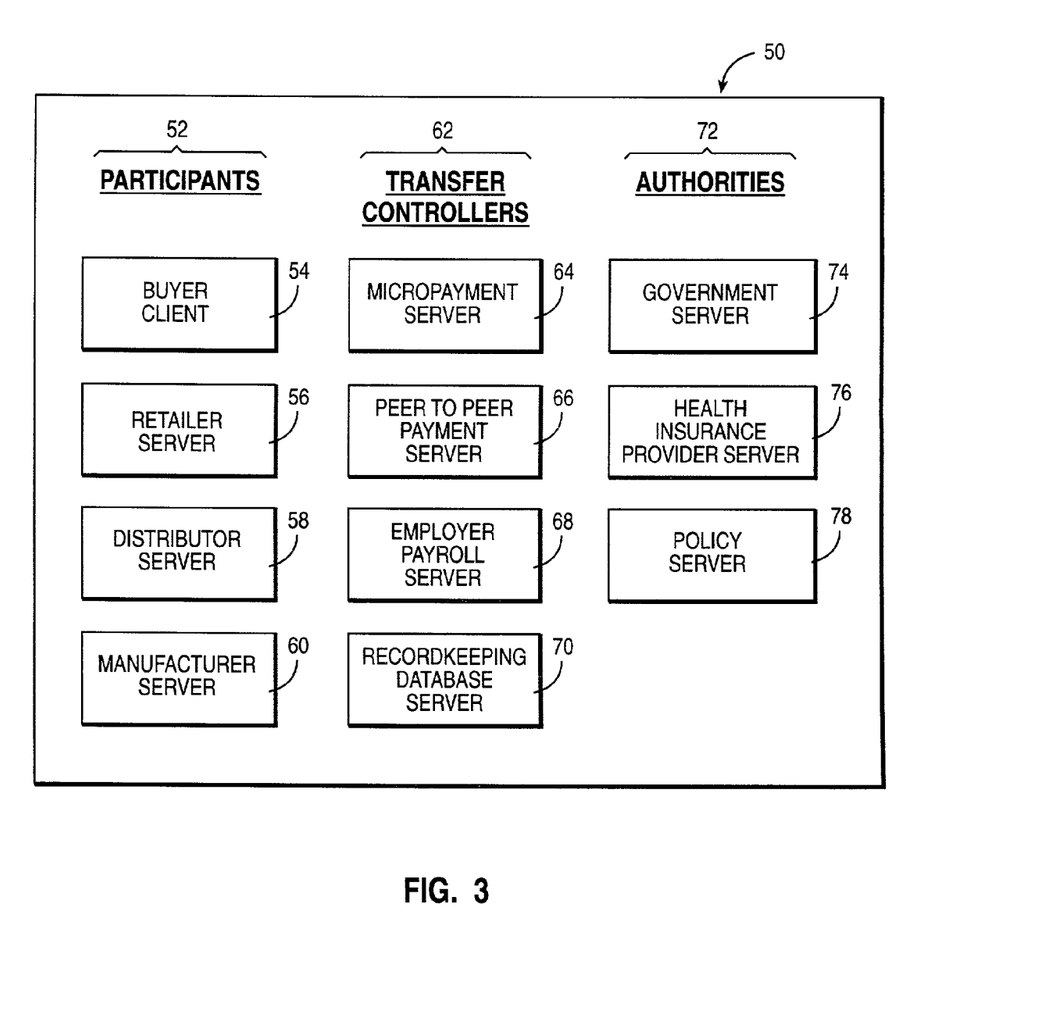
FIG. 3 depicts a block diagram of multiple types of servers and clients that may be utilized to promote and control healthful food consumption in accordance with the method, system, and program of the present invention.

Referring now to FIG. 3, there is depicted a block diagram of multiple types of servers and clients that may be utilized to promote and control healthful food consumption in accordance with the method, system, and program of the present invention. As illustrated, multiple client and server elements 50 are divided according to category. In the present embodiment categories include, but are not limited to, participants 52, transfer controllers 62, and authorities 72.

Participants 52 advantageously include all levels of people, businesses, and corporations involved in food production, sales and consumption. In the present embodiment, participants 52 include, but are not limited to, a buyer client 54, a retailer server 56, a distributor server 58, and a manufacturer server 60. Buyer client 54 advantageously represents a system for monitoring food purchases and food consumption. Retailer server 56, distributor server 58, and manufacturer server 60 advantageously monitor the purchase of consumable items sold by retailers, distributors and manufacturers.

Transfer controllers 62 advantageously include all levels of controllers that may be provided for transferring, storing and recording monetary incentives for healthful food consumption for at least one of participants 52. In the present embodiment, transfer controllers 62 include, but are not limited to, a micropayment server 64, a peer-to-peer payment server 66, an employer payroll server 68, and a recordkeeping database server 70. Micropayment server 64 advantageously includes an accounting system for internal monetary incentives that are spendable by a consumer for products and services offered by the authority granting the incentive. Peer-to-peer payment server 66 advantageously includes an accounting system for external electronic incentives that are spendable by a consumer for products and services offered external to the authority granting the incentive. Recordkeeping database server 70 advantageously monitors all transfers of electronic incentives for healthful food consumption.

Employer payroll server 68 advantageously includes an accounting system for employee pay that may be supplemented with electronic incentives for healthful food consumption. In particular, employers are finding that paying for preventative measures, such as health plans that provide annual health check-ups, pay for themselves in a reduction of sick days and health issues. According to one advantage of the present invention, employers may pay for a health plan that provides incentives, to the employer and/or directly to the employee, for healthy food consumption.

Authorities 72 advantageously include all levels of government, policy setting groups, and health care insurance providers that set policy and standards for healthful foods and provide electronic incentives in response to healthful food consumption by at least one of participants 52. In the present example, authorities 72 specifically includes a government server 74, a health insurance provider server 76, and a policy server 78. Government server 74 preferably designates healthy food standards by governmental groups, such as the Food and Drug Administration (FDA). Health insurance provider server 76 preferably designates health food standards for health insurance providers. Policy server 78 preferably designates health food standards by other policy setting groups, such as university scientists that study nutrition.

Health Habit Incentive Context

Figure 4:
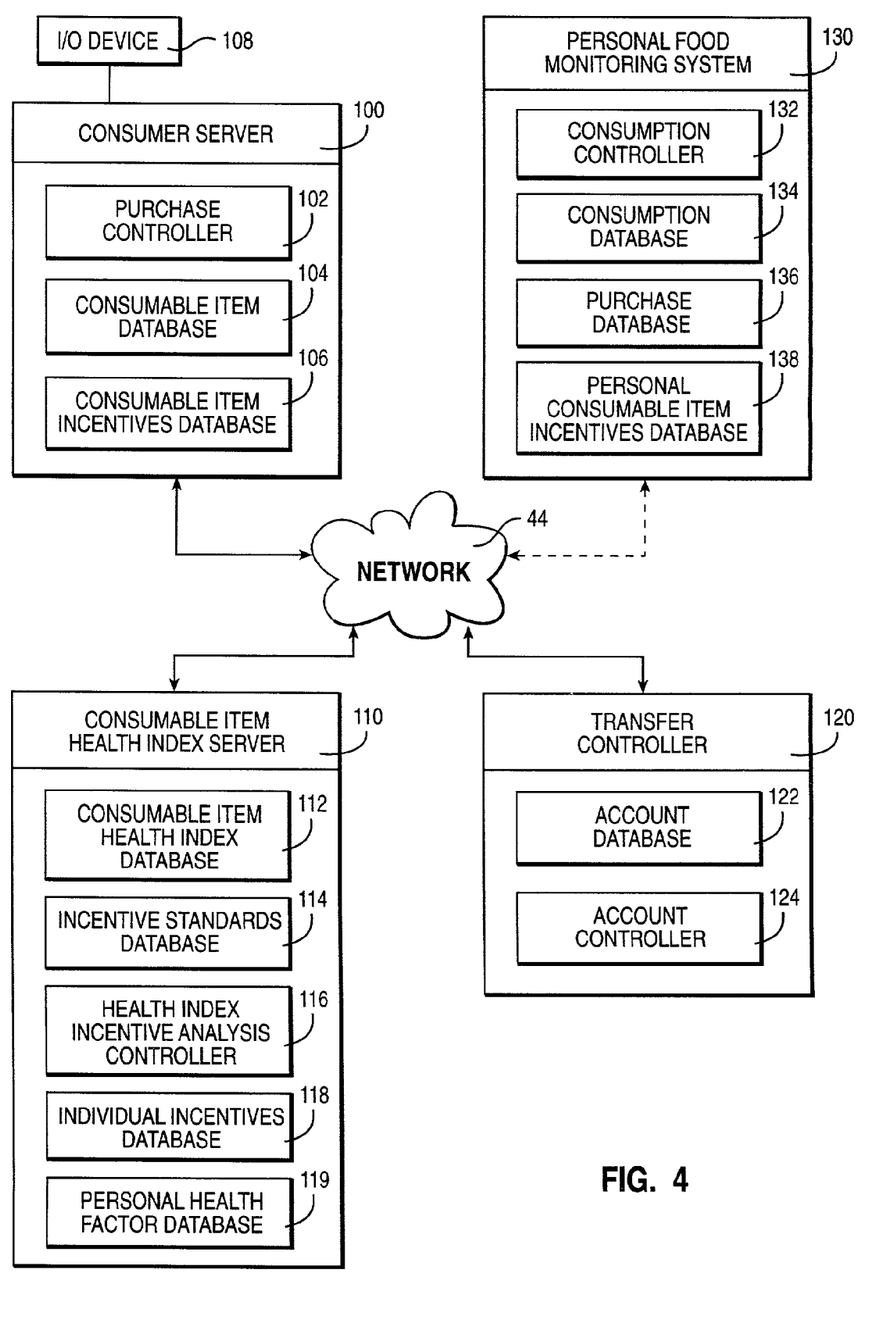
FIG. 4 illustrates a block diagram of a healthful food incentive system in accordance with the method, system, and program of the present invention.

With reference now to FIG. 4, there is depicted a block diagram of a healthful food incentive system in accordance with the method, system, and program of the present invention. As illustrated, multiple client and server systems are communicatively connected via network 44.

A consumer server 100 preferably monitors food purchases by consumers. In the example, purchase controller 102 monitors which consumer is purchasing which food items. Purchase controller 102 also controls storage of purchase records according to consumer in a consumable item database 104. Advantageously, each consumer may be identified according to an alphanumeric, graphical, or other distinguishable indicator.

In addition, purchase controller 102 controls transmission of food purchase records to a consumable item health index server 110. Consumable item health index server 110 may return monetary incentives for the food item to consumer server 100. Purchase controller 102 may apply the incentive automatically to a cost for the food item or may display the type of incentive and amount to the consumer where the incentive is to be applied later.

In particular, as purchase decisions are being made, whether in the aisle where food is placed or in a restaurant, the consumer is preferably provided with a display or other output that compares food items. In particular, consumer server 100 preferably includes an input/output (I/O) device 108 that displays comparisons of products for consumers while purchase decisions are being made. In addition, a personal food monitoring system 130 may request health indexes according to a product identifier and compare multiple product health indexes for a consumer.

According to a further advantage of the present invention, food retailers may pre-request, for food items in stock, some types of electronic incentives that are provided for healthful products independent of the actual consumer. Pre-requested incentives may be stored in consumable item incentives database 106 according to food item and made available when the associated food item is purchased.

In particular, consumer server 100 may include additional peripherals, such as a scanner, that detect an identifier for a food item and transmit that identifier to consumer server 100. Further, advantageously, food items may include a scannable identifier that identifies an instant incentive to be returned to the consumer from consumer server 100. Where an instant incentive is provided to a consumer from consumer server 100, a record of the incentive is preferably stored in consumable item incentives database 106 and a request for the incentive to be redeemed is transmitted to the authority providing the incentive, such as consumable item health index server 110.

A personal food monitoring system 130 preferably monitors the food intake of a consumer by monitoring the types of meals ordered, the recipes utilized for meals, and by receiving inputs from the consumer as to what food items were eaten. First, personal food monitoring system 130 may monitor the food items purchased by consumers at restaurants and store the food orders within a purchase database 136. In addition, a consumer may access a recipe or store recipes within personal food monitoring system 130 wherein the food items included in a recipe are stored within consumption database 134 when a consumer indicates that the recipe has been utilized to make a meal. Further, a list of food items purchased by a consumer at a market are advantageously transmitted from consumer server 100 to personal food monitoring system 130 and stored in purchase database 136. A consumer may then select from the list of purchased items to indicate when the consumer consumes the item; a record of the consumption of a food item is stored in consumption database 134.

Additional peripherals may be associated with personal food monitoring system 130 that allow for monitoring food consumption. For example, a scale detects a type of food item being weighed and the weight thereof such that personal food monitoring system 130 may monitor the consumption of home-grown food items.

Further, personal food monitoring system 130 may include features for food monitoring as described in U.S. Pat. No. 6,618,062, issued Sep. 9, 2003, U.S. Pat. No. 6,859,215, issued Feb. 22, 2005, and U.S. Pat. No. 6,646,659, issued Nov. 11, 2003, herein incorporated by reference.

Moreover, personal food monitoring system 130 may include features for health and exercise monitoring as described in U.S. Pat. No. 6,450,955, issued Sep. 17, 2002 U.S. Pat. No. 6,440,068, issued Aug. 27, 2002, and U.S. Pat. No. 6,601,016, issued Jul. 29, 2003, herein incorporated by reference. For example, personal food monitoring system 130 may monitor health attributes of a consumer, such as pulse, blood pressure, secretion, perspiration, weight, body fat, stress, carpal movement, distance, respiration, glucose level, and other indicators of health or well being. In addition, personal food monitoring system 130 may monitor exercise performed by a consumer by monitoring health attributes and receiving indicators from exercise equipment as to the intensity of exercise.

Advantageously, personal food monitoring system 130 may remain connected to network 44 or may periodically connect to network 44 to exchange information via network 44 with consumer server 100, consumable item health index server 110 and transfer controller 120.

Personal food monitoring system 130 may transmit food consumption indications according to restaurant purchases, recipe items, and other food consumption indications to consumable item health index server 110. Consumable item health index server 110 advantageously may return electronic incentives or records of electronic incentives in response to a consumer's food consumption. Electronic incentives may be stored within a personal consumable item incentives database 138. In particular, where an incentive is a discount on future food item purchases, such as an electronic coupon, the incentive is stored in personal consumable item incentives database 138 and may be transmitted to consumer server 100 or another server system for redemption.

Consumable item health index server 110 includes a consumable item health index database 112 in which food items are specified according to health index components and the health index components are assigned values. For example, a slice of bread may be specified with a health index component of a grain with a value from 0 to 10, depending on the kind of bread.

In addition, consumable item health index server 110 includes an incentive standards database 114 that includes generic healthful food standards. In particular, health index values are assigned incentives. Where the government is providing rebates, electronic coupons, or other incentives for healthful food purchases, incentive standards database 114 preferably sets the standards for such incentives.

In particular, incentive standards may be specified according to an individual consumer or groups of consumers. In particular, where incentive standards are specified by an entity, such as a health insurance provider, the health and exercise information of individual consumers may be kept confidential and only utilized to determine incentives, not to prohibit a consumer from making purchases, receiving insurance, or other forms of discrimination based on health. Governments and other policy setting groups preferably specify incentive standards according to groups of consumers, such as groups according to age or health factors.

Health preferences and limitations may be determined according to an individual consumer or group of consumer by analyzing individual health histories, family health histories, food intake, exercise routines, medications, and other health related factors in addition to multiple dietary plans to determine dietary preferences and limitations. Further, incentive standards may be time dependent, such that incentives are greater for consumption of a particular food item during a designated lunch time and less for consumption of the particular food item during other periods of time.

Additionally, incentive standards may include food consumption thresholds, where after a consumer has consumed beyond the food consumption threshold, incentives are adjusted and may become negative incentives. For example, where a consumer is allowed a particular number of calories each day, negative incentives may be given for consumption beyond the threshold of calories, unless additional exercise or medical problems necessitate an increase in daily calories.

Records of food items that have been purchased, prepared, and consumed by a particular consumer are received at consumable item health index server 110 to determine whether an incentive is available. Health index incentive analysis controller 116 determines a health index for a food item from consumable item health index database 112 and then determines if an incentive is available according to the item's health index within incentive standards database 114, where incentives are specified according to consumer by health information contained for each consumer in a personal health factor database 119. In particular, food consumption, health attributes, and exercise indicators for each consumer may be received from personal food monitoring system 130 or another monitoring system, and stored in personal health factor database 119. For example, a consumer with high blood pressure indicated in personal health factor database 119 will receive incentives to consume items that are low in salt.

Incentives may be transmitted to consumer server 100 for immediate redemption or personal food monitoring system for future redemption. Further, records of incentives may be stored in individual incentives database 118 according to consumer for future redemption or use.

In particular, incentives may be in small monetary unit increments, such that a single incentive may not adjust food or health insurance costs by much, but accumulated over time the incentives will adjust costs by more definable amounts. For example, an incentive of 10 cents may not be significant enough for a consumer to choose a healthy food over a less healthy one. However, a health insurance provider may provide a yearly incentive of a reduced insurance rate for achieving a particular yearly cumulative incentive amount. In particular, where a health insurance adjustment is provided and an employer pays for insurance, the health insurance provider may transfer an incentive to an employer payroll server to supplement the income of an employee in response to healthful food choices by that employee. Additionally, the company may offer an incentive through the employer payroll server for healthful food choices.

Advantageously, a transfer controller 120 includes an account database 122 for storing electronic incentives according to consumer and an account controller for controlling input to and output from account database 122. Transfer controller 120 may provide an internal storage account for incentives, such as those incentives provided by a health care provider that may be redeemed for adjustments in health care costs. Alternatively, transfer controller 120 may provide an external storage account for incentives, such as those incentives provided by an authority, that may be spent by the consumer on external products and services. Further, transfer controller 120 may be provided as an employer payroll server to which incentives may be transferred to add to employee pay.

Figure 5:
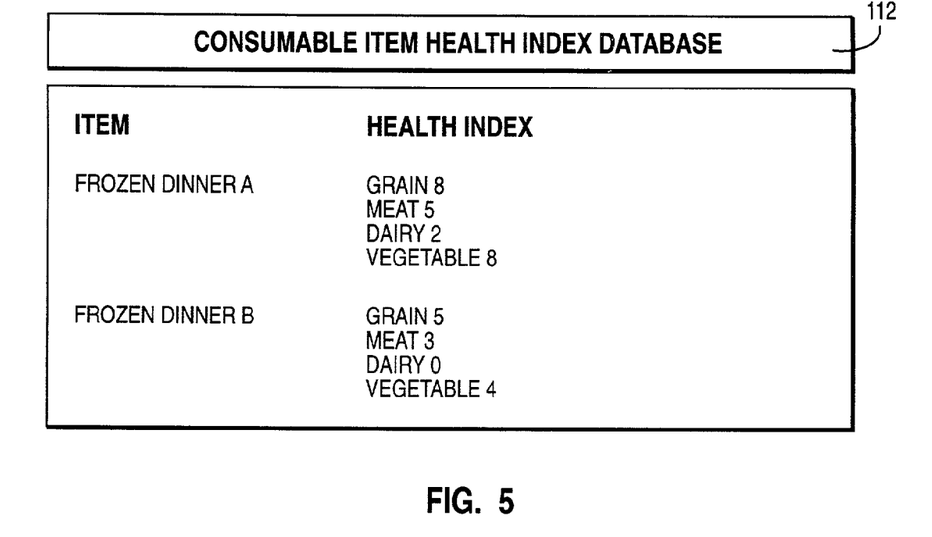
FIG. 5 depicts a consumable item health index database in accordance with the method, system, and program of the present invention.

Referring now to FIG. 5, there is illustrated a consumable item health index database in accordance with the method, system, and program of the present invention. As illustrated, a consumable item health index database 112 includes a consumable item that is broken down into health index components and values. In the present example, health index components for "frozen dinner A" includes grains, meat, dairy, and vegetables. In alternate embodiments, alternate types of health index components may be included. In addition, health index components may include unhealthy component ratings, such as unhealthy fats.

Health index breakdowns may be assigned by a government agency, entity, consumer, retailer, distributor or manufacturer. Currently, any food purveyor is responsible for providing nutritional information about the product. Such information may be stored in database 112 for reference.

Figure 6:
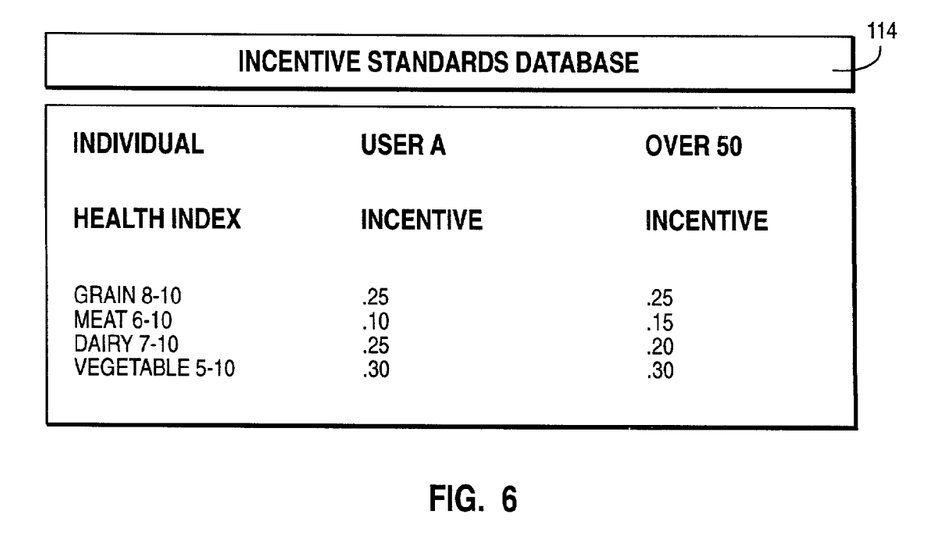
FIG. 6 illustrates an incentive standards database in accordance with the method, system, and program of the present invention.

With reference now to FIG. 6, there is depicted an incentive standards database in accordance with the method, system, and program of the present invention. An incentive standards database 114 includes health index incentives associated with individual consumer or groups of consumers. For example, an incentive for consumers over a particular age may be distinguished from an incentive for consumers under a particular age.

In the present example, grain index between 8 and 10 are given an incentive of 0.25. Incentive amounts may represent monetary amounts, percentages, cumulative amounts, and other units. For example, where incentives are cumulative amounts, a consumer may accumulate a particular level of cumulative amounts to receive a discount or other monetary incentive.

Advantageously, multiple authorities and entities may access a single consumable item health index server to provide incentives. Thus, each of the authorities and entities may utilize the health indexes to determine incentives.

Figure 7:
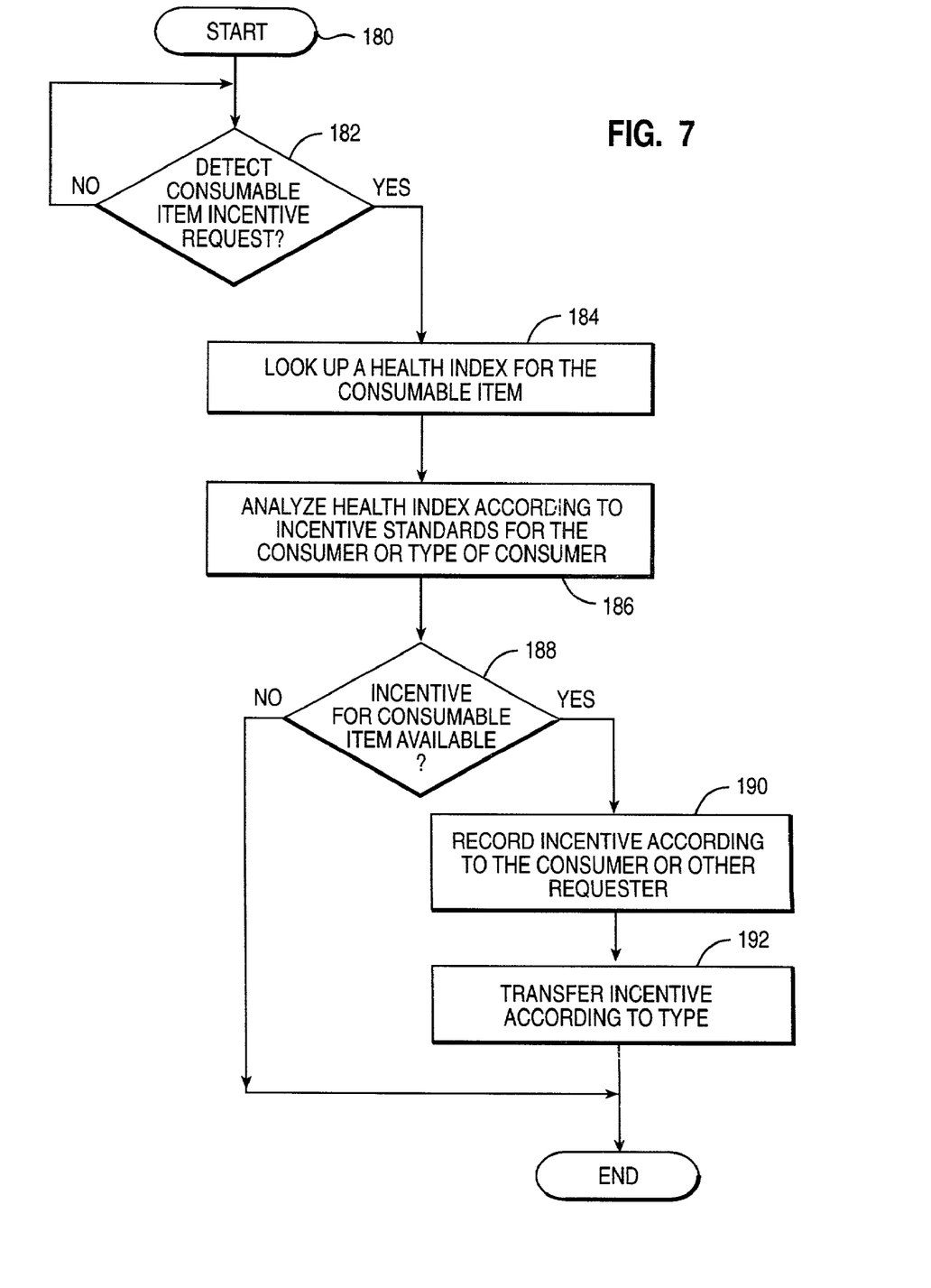
FIG. 7 depicts a high level logic flowchart of a process and program for determining incentives for healthful foods in accordance with the method, system, and program of the present invention.

Referring now to FIG. 7, there is illustrated a high level logic flowchart of a process and program for determining incentives for healthful foods in accordance with the method, system, and program of the present invention. As depicted, the process starts at block 180 and thereafter proceeds to block 182.

Block 182 depicts a determination as to whether or not a consumable item incentive request is received. If a request is not received, then the process iterates at block 182. If a request is received, then the process passes to block 184.

Block 184 illustrates looking up a health index for the consumable item. Next, block 186 depicts analyzing the health index according to incentive standards for the consumer or type of consumer; and the process passes to block 188.

Block 188 depicts a determination as to whether or not an incentive for the consumable item is available. If an incentive is not available, then the process ends. If an incentive is available, then the process passes to block 190.

Block 190 illustrates recording the incentive according to the consumer or requester. Next, block 192 depicts transferring the incentive according to type of incentive to the appropriate system; and the process ends. For example, cumulative incentives may be transferred to a transfer server to accumulate.

Figure 8:
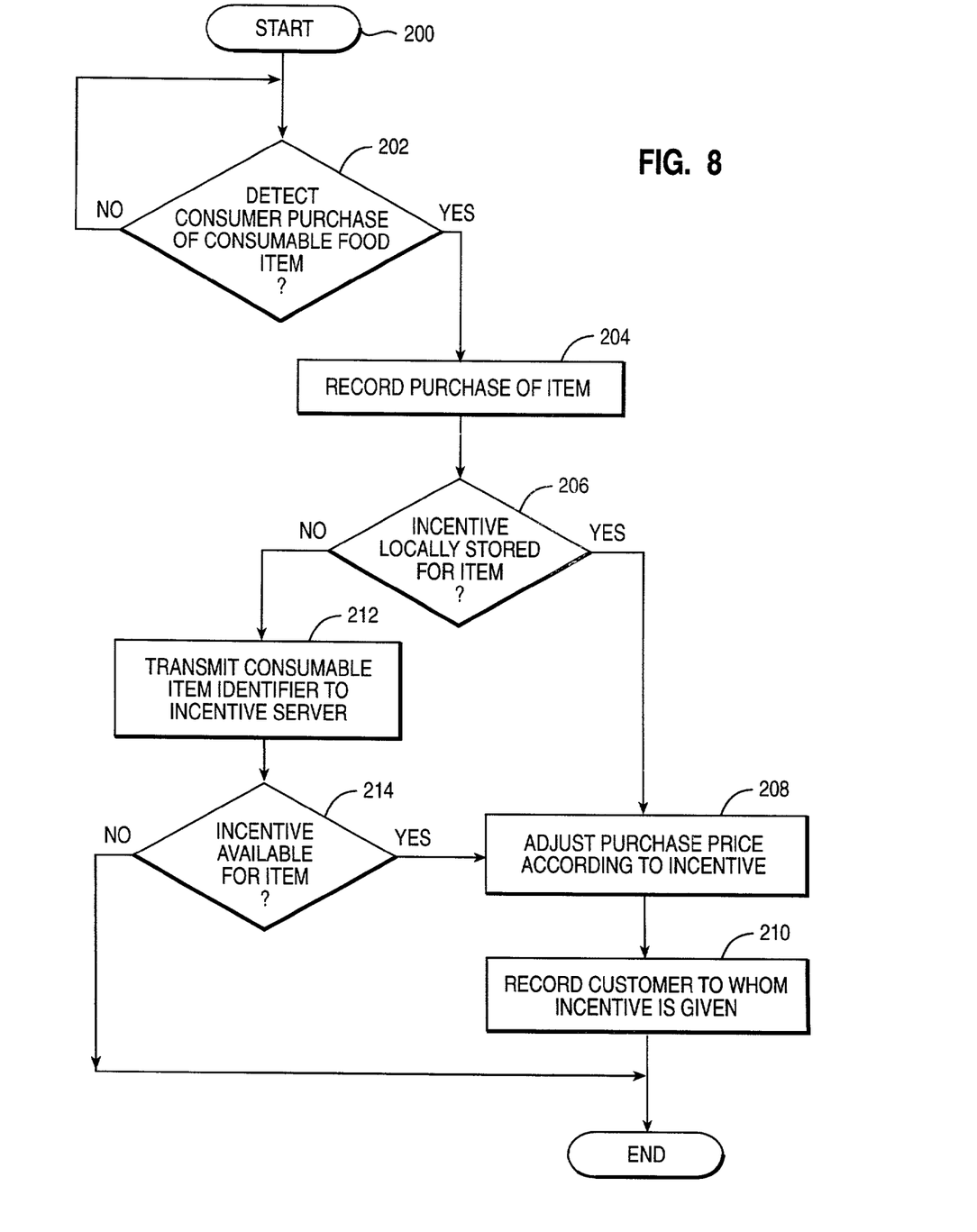
FIG. 8 illustrates a high level logic flowchart of a process and program for providing incentives for healthful food item purchases in accordance with the method, system, and program of the present invention.

With reference now to FIG. 8, there is depicted a high level logic flowchart of a process and program for providing incentives for healthful food item purchases in accordance with the method, system, and program of the present invention. As illustrated, the process starts at block 200 and thereafter proceeds to block 202.

Block 202 depicts a determination as to whether or not a consumer purchase of a consumable food item at a retailer or other food provider is detected. If a purchase is not detected, then the process iterates at block 202. If a purchase is detected, then the process passes to block 204. Block 204 illustrates recording a purchase of the item; and the process passes to block 206.

Block 206 illustrates a determination as to whether or not an incentive is stored locally for the item. Incentives may be retrieved by a retailer for food products to speed up the transfer of incentives at the point of sale. If an incentive is not locally stored for the item, then the process passes to block 212. If an incentive is stored for the item, then the process passes to block 208.

Block 212 depicts transmitting the consumable item identifier to the incentive server. Next, block 214 illustrates a determination as to whether or not an incentive is available for the item. If an incentive is not available, then the process ends. If an incentive is available, then the process passes to block 208.

Block 208 illustrates adjusting the purchase price according to the incentive. Next, block 210 illustrates recording the consumer to whom the incentive is given; and the process ends.

While the invention has been particularly shown and described with reference to a preferred embodiment, it will be understood by those skilled in the art that various changes in form and detail may be made therein without departing from the spirit and scope of the invention.

What is claimed is:

1. A method for encouraging healthy habits by an individual, said method comprising the steps of:
   tracking, using at least one computer system communicatively connected to a network, an actual purchase of a particular consumable item from a vendor by an individual for potential consumption;
   determining, at said at least one computer system, a plurality of separate health index values each associated with a separate one of a plurality of health index components for consumption of said particular consumable item;
   selecting, at said at least one computer system, a monetary electronic incentive for said individual based on said plurality of separate health index values matching at least one health index value requirement specified in a database of electronic incentives specified for said individual according to at least one factor from among food intake by said individual based on at least one of an ordered meal and a recipe for a meal previously reported to said at least one computer system and exercise performed by said individual previously detected by said at least one computer system; and
   automatically transferring said monetary electronic incentive via said network from said at least one computer system to an account provider system which stores said monetary electronic incentive in an electronic account for said individual.

2. The method for encouraging healthy habits according to claim 1, said step of tracking, using at least one computer system communicatively connected to a network, an actual purchase of a particular consumable item further comprising the step of:
   detecting, at said at least one computer system, from a scanner system for said vendor that scans and identifies said particular consumable item, an identifier for said particular consumable item.

3. The method for encouraging healthy habits according to claim 1, said step of tracking, using at least one computer system communicatively connected to a network, an actual purchase of a particular consumable item further comprising the step of:
   receiving, at said at least one computer system via said network, from a restaurant meal ordering system an identifier of said consumable item ordered by said individual.

4. The method for encouraging healthy habits according to claim 1, said step of tracking, using at least one computer system communicatively connected to a network, an actual purchase of a particular consumable item further comprising the step of:
   receiving, at said at least one computer system, an identifier of said particular consumable item from a food monitoring system for said individual.

5. The method for encouraging healthy habits according to claim 1, said step of selecting, at said at least one computer system, a monetary electronic incentive for said individual further comprising the step of:
   assigning, at said at least one computer system from a separate authority server system, said monetary electronic incentive of at least one from among an electronic coupon, a rebate, an incentive, a cumulative amount, and a cost reduction.

6. The method for encouraging healthy habits according to claim 1, said step of selecting, at said at least one computer system, a monetary electronic incentive for said individual further comprising the step of:
   assigning, at said at least one computer system from a separate authority server system via said network, said monetary electronic incentive from at least one authority from among a plurality of levels of government and a health care insurance provider.

7. The method for encouraging healthy habits according to claim 1, said method further comprising the step of:
   specifying said monetary electronic incentive for said individual within said database of electronic incentives according to at least one of a health history and a current health condition of said individual.

8. The method for encouraging healthy habits according to claim 1, said method further comprising the step of:
   specifying said monetary electronic incentive for said individual within said database of electronic incentives according to a particular incentive standard assigned to a type of group, wherein said individual meets a characteristic of said type of group.

9. The method for encouraging healthy habits according to claim 1, said method further comprising the step of:
   specifying said monetary electronic incentive for said individual within said database of electronic incentives according to a time of day when said particular consumable item is consumed by said individual.

10. A system for encouraging healthy habits by an individual, said system comprising:
    a plurality of server systems communicatively connected via a network;
    at least one first server system from among said plurality of server systems operative to track an actual purchase of a particular consumable item by an individual from a vendor for potential consumption;
    said at least one first server system operative to determine, from at least one second server system from among said plurality of server systems, a plurality of separate health index values each associated with a separate one of a plurality of health index components for consumption of said particular consumable item;
    said at least one first server system operative to select an electronic incentive for said individual based on said plurality of separate health index values matching at least one health index value requirement specified in a database of electronic incentives accessed from at least one third server system from among said plurality of server systems and specified for said individual according to at least one factor from among food intake by said individual based on at least one of an ordered meal and a recipe for a meal previously reported to said server system and exercise performed by said individual previously detected by said server system; and
    said at least one first server system operative to automatically transfer said monetary electronic incentive via said network to at least one account provider system from among said at plurality of server systems which stores said electronic incentive in an electronic account for said individual.

11. The system for encouraging healthy habits according to claim 10, said at least one server system operative to track an actual purchase of a particular consumable item further operative to detect from a scanner system for said vendor that scans and identifies said particular consumable item, an identifier for said particular consumable item.

12. The system for encouraging healthy habits according to claim 10, said at least one server system operative to track an actual purchase of a particular consumable item further, from a restaurant meal ordering system, an identifier of said consumable item ordered by said individual.

13. The system for encouraging healthy habits according to claim 10, said at least one server system operative to track an actual purchase of a particular consumable item further operative to receive an identifier of said particular consumable item from a food monitoring system for said individual.

14. The system for encouraging healthy habits according to claim 10, said at least one server system operative to select a monetary electronic incentive for said individual according to said health factor further operative to assign, at said at least one first server system from a separate authority server system from among said plurality of server systems, said monetary electronic incentive of at least one from among an electronic coupon, a rebate, an incentive, a cumulative amount, and a cost reduction.

15. The system for encouraging healthy habits according to claim 10, said at least one server system operative to select a monetary electronic incentive for said individual according to said health factor further operative to assign, at said at least one first server system from a separate authority server system from among said plurality of server systems, said monetary electronic incentive from at least one authority from among a plurality of levels of government and a health care insurance provider.

16. The system for encouraging healthy habits according to claim 10, said at least one server system further operative to specify said monetary electronic incentive for said individual within said database of electronic incentives according to at least one of a health history and a current health condition of said individual.

17. The system for encouraging healthy habits according to claim 10, said at least one server system further operative to specify said monetary electronic incentive for said individual within said database of electronic incentives according to a particular incentive standard assigned to a type of group, wherein said individual meets a characteristic of said type of group.

18. The system for encouraging healthy habits according to claim 10, said at least one server system further operative to specify said monetary electronic incentive for said individual within said database of electronic incentives according to a time of day when said particular consumable item is consumed by said individual.

19. A program for encouraging healthy habits by an individual, residing on a non-transitory computer readable storage medium comprising instructions which when executed on a computer system cause said computer system to:
enable tracking of an actual purchase of a particular consumable item from a vendor by an individual;
determine a plurality of separate health index values each associated with a separate one of a plurality of health index components for consumption of said particular consumable item;
select a monetary electronic incentive for said individual based on said plurality of separate health index values matching at least one health index value requirement specified in a database of electronic incentives specified for said individual according to at least one factor from among food intake reported by said individual based on at least one of an ordered meal and a recipe for a meal and previously detected exercise performed by said individual; and
automatically transfer said monetary electronic incentive via said network to an account provider system which stores said monetary electronic incentive in an account for said individual.

20. The program for encouraging healthy habits according to claim 19, said instructions which when executed on a computer system further causing said computer system to:
enable detection, from a scanner system for said vendor that scans and identifies said particular consumable item, an identifier for said particular consumable item.

21. The program for encouraging healthy habits according to claim 19, said instructions which when executed on a computer system further causing said computer system to:
enable receipt, from a restaurant meal ordering system, an identifier of said consumable item ordered by said individual.

22. The program for encouraging healthy habits according to claim 19, said instructions which when executed on a computer system further causing said computer system to:
enable receipt of an identifier of said particular consumable item from a food monitoring system for said individual.

23. The program for encouraging healthy habits according to claim 19, said instructions which when executed on a computer system further causing said computer system to:
assign, as directed by a separate authority server system, said monetary electronic incentive of at least one from among an electronic coupon, a rebate, an incentive, a cumulative amount, and a cost reduction.

24. The program for encouraging healthy habits according to claim 19, said instructions which when executed on a computer system further causing said computer system to:
assign, as directed by a separate authority server system, said monetary electronic incentive from at least one authority from among a plurality of levels of government and a health care insurance provider.

25. The program for encouraging healthy habits according to claim 19, said instructions which when executed on a computer system further causing said computer system to:
specify said monetary electronic incentive for said individual within said database of electronic incentives according to at least one of a health history and a current health condition of said individual.

26. The program for encouraging healthy habits according to claim 19, said instructions which when executed on a computer system further causing said computer system to:
specify said monetary electronic incentive for said individual within said database of electronic incentives according to a particular incentive standard assigned to a type of group, wherein said individual meets a characteristic of said type of group.

27. The program for encouraging healthy habits according to claim 19, said instructions which when executed on a computer system further causing said computer system to:
specify said monetary electronic incentive for said individual within said database of electronic incentives according to a time of day when said particular consumable item is consumed by said individual.

* * * * *